(12) United States Patent
Breuer et al.

(10) Patent No.: US 12,186,455 B2
(45) Date of Patent: Jan. 7, 2025

(54) COMPOSITIONS AND METHODS FOR PROMOTING PATENCY OF VASCULAR GRAFTS

(71) Applicant: Yale University, New Haven, CT (US)

(72) Inventors: Christopher Breuer, New Haven, CT (US); Themis Kyriakides, New Haven, CT (US); Jason Roh, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 358 days.

(21) Appl. No.: 17/713,766

(22) Filed: Apr. 5, 2022

(65) Prior Publication Data

US 2022/0226542 A1    Jul. 21, 2022

Related U.S. Application Data

(60) Continuation of application No. 15/850,364, filed on Dec. 21, 2017, now abandoned, which is a division of application No. 12/811,676, filed as application No. PCT/US2009/030407 on Jan. 8, 2009, now Pat. No. 9,855,370.

(60) Provisional application No. 61/010,406, filed on Jan. 8, 2008.

(51) Int. Cl.
| | |
|---|---|
| A61L 27/50 | (2006.01) |
| A61K 38/19 | (2006.01) |
| A61L 27/18 | (2006.01) |
| A61L 27/54 | (2006.01) |
| A61F 2/06 | (2013.01) |

(52) U.S. Cl.
CPC ............ *A61L 27/507* (2013.01); *A61L 27/18* (2013.01); *A61L 27/54* (2013.01); *A61F 2/06* (2013.01); *A61K 38/195* (2013.01); *A61L 2300/426* (2013.01); *A61L 2300/604* (2013.01)

(58) Field of Classification Search
None
See application file for complete search history.

(56) References Cited

U.S. PATENT DOCUMENTS

| | | |
|---|---|---|
| 5,459,128 A | 10/1995 | Rollins |
| 5,716,394 A | 2/1998 | Bruchman |
| 5,922,554 A | 7/1999 | Fielding |
| 6,441,004 B1 | 8/2002 | Faull |
| 6,517,858 B1 | 2/2003 | Le Moel |
| 6,833,387 B1 | 12/2004 | Faull |
| 7,482,434 B2 | 1/2009 | Gudas |
| 7,611,532 B2 | 11/2009 | Bates |
| 11,541,149 B2 | 1/2023 | Breuer |
| 2002/0125613 A1 | 9/2002 | Cominsky |
| 2002/0187184 A1 | 12/2002 | Golomb |
| 2003/0013686 A1 | 1/2003 | Golomb |
| 2003/0064965 A1 | 4/2003 | Richter |
| 2003/0082148 A1 | 5/2003 | Ludwig |
| 2004/0044405 A1 | 3/2004 | Wolff |
| 2004/0063654 A1 | 4/2004 | Davis |
| 2004/0071861 A1 | 4/2004 | Mandrusov |
| 2005/0058692 A1 | 3/2005 | Hai-Quan |
| 2005/0120951 A1 | 6/2005 | Spencer |
| 2005/0124534 A1 | 6/2005 | Noble |
| 2005/0143817 A1 | 6/2005 | Hunter |
| 2005/0163821 A1 | 7/2005 | Sung |
| 2005/0220848 A1 | 10/2005 | Bates |
| 2006/0045905 A1 | 3/2006 | Ozeki |
| 2006/0217437 A1 | 9/2006 | Burmester |
| 2007/0141042 A1 | 6/2007 | Franano |
| 2008/0091234 A1 | 4/2008 | Kladakis |
| 2008/0097575 A1 | 4/2008 | Cottone |
| 2009/0012607 A1 | 1/2009 | Kim |
| 2009/0043378 A1 | 2/2009 | Cheng |
| 2009/0098183 A1 | 4/2009 | Detamore |
| 2010/0092534 A1 | 4/2010 | Hezi-Yamit |
| 2010/0129414 A1 | 5/2010 | Dolan |
| 2010/0292773 A1 | 11/2010 | Schmid |
| 2010/0303889 A1 | 12/2010 | Breuer |
| 2011/0281358 A1 | 11/2011 | Breuer |
| 2013/0013083 A1 | 1/2013 | Blum |
| 2014/0072951 A1 | 3/2014 | Johnson |
| 2014/0147484 A1 | 5/2014 | Breuer |

(Continued)

FOREIGN PATENT DOCUMENTS

| | | |
|---|---|---|
| CN | 101553244 | 10/2009 |
| EA | 200600470 | 2/2007 |

(Continued)

OTHER PUBLICATIONS

Alexi-Meskishvili, et al., "Optimal conduit size for extracardiac Fontan operation", Eur. J. Cardiothorac. Surg., 18:690-5 (2000).

(Continued)

*Primary Examiner* — Daniel C Gamett
(74) *Attorney, Agent, or Firm* — PABST PATENT GROUP LLP

(57) ABSTRACT

Methods for increasing the patency of biodegradable, synthetic vascular grafts are provided. The methods include administering one or more cytokines and/or chemokines that promote outward tissue remodeling of the vascular grafts and vascular neotissue formation. The disclosed methods do not require cell seeding of the vascular grafts, thus avoiding many problems associated with cell seeding. Biodegradable, polymeric vascular grafts which provide controlled release of cytokines and/or chemokines at the site of vascular graft implantation are also provided.

24 Claims, 6 Drawing Sheets

(56) References Cited

U.S. PATENT DOCUMENTS

| | | |
|---|---|---|
| 2014/0272225 A1 | 9/2014 | Johnson |
| 2014/0358217 A1 | 12/2014 | Stankus |
| 2016/0136326 A1 | 5/2016 | Fisher |

FOREIGN PATENT DOCUMENTS

| | | |
|---|---|---|
| EP | 1066378 | 1/2001 |
| RU | 2452517 | 3/2011 |
| RU | 2440128 | 1/2012 |
| WO | 1997028262 | 8/1997 |
| WO | 9951741 | 10/1999 |
| WO | 2000012497 | 3/2000 |
| WO | 2000061576 | 10/2000 |
| WO | 01010421 | 2/2001 |
| WO | 2002102432 | 12/2002 |
| WO | 2004016606 | 2/2004 |
| WO | 2004050659 | 6/2004 |
| WO | 2004080982 | 9/2004 |
| WO | 2004112710 | 12/2004 |
| WO | 2005013915 | 2/2005 |
| WO | 2005063965 | 7/2005 |
| WO | 2006026306 | 3/2006 |
| WO | 2006099332 | 9/2006 |
| WO | 2007059253 | 5/2007 |
| WO | 2008009062 | 1/2008 |
| WO | 2008047198 | 4/2008 |
| WO | 2009089324 | 7/2009 |
| WO | 2011146046 | 11/2011 |
| WO | 2014197790 | 12/2014 |

OTHER PUBLICATIONS

American Heritage Medical Dictionary, "Definition of Patency", Medical dictionary, Houghton Mifflin Co, (2004).
Bermudez, et al., "Late results of the peel operation for replacement of failing extracardiac conduits", Ann. Thorac. Surg., 77:881-8 (2004).
Brennan, et al., "Tissue-engineered vascular grafts demonstrate evidence of growth and development when implanted in a juvenile animal model", Annals of Surgery, 248(3):370-377 (2008).
Cho, et al., "Enhancement of in vivo endothelialization of tissue-engineered vascular grafts by granulocyte colony-stimulation factor", J Biomed Mater Res., 76(2):252-63 (2006).
Cleveland, et al., "Failure of cryopreserved homograft valved conduits in the pulmonary circulation", Circulation, 86(suppl II):II150-3 (1992).
Conte, "The ideal small arterial substitute: a search for the Holy Grail?", FASEB, 12:43-5 (1998).
Dearani, et al., "Late follow-up of 1095 patients undergoing operation for complex congenital heart disease utilizing pulmonary ventricle to pulmonary artery conduits", Ann. Thorac. Surg., 75:399-411 (2003).
Duncan, et al., "TGFβR1 inhibition blocks the formation of stenosis in tissue-engineered vascular grafts", J Am Coll Cardiol., 65(5):512-4 (2015).
Ferrara, et al., "Recombinant renewable polyclonal antibodies", mAbs, 7(1):32-41 (2015).
Fontan and Baudet, "Surgical repair of tricuspid atresia", Thorax, 26(3):240-8 (1971).
Fontan, et al., "Outcome after a "perfect" Fontan operation", Circulation, 81:1520-36 (1990).
Fu, et al., "SMI6, an orally active TGF-beta type I receptor inhibitor prevents myofibroblast induction and vascular fibrosis in the rat carotid injury model", Arteriosclerosis Thrombosis and Vascular Biology, 28(4): 665-671 (2008).
Giannico, et al., "Clinical outcome of 193 extracardiac Fontan patients: the first 15 years", J. Amer. College Card., 47(10):2065-73 (2006).
Hager, et al., "Long-term survival of patients with univentricular heart not treated surgically" J. Tnorac. Cardiovasc. Surg., 123:1214-7 (2002).

Hagihara, et al., "Vascular protection by chloroquine during brain tumor therapy with Tf-CRM107", Cancer Research, 60(2):230-234 (2000).
Haliotis, et al., "Chédiak-Higashi gene in humans I. Impairment of natural-killer function", J. Exp. Med., 151:1039-48 (1980).
Hibino, et al., "A critical role for macrophages in neovessel formation and the development of stenosis in tissue-engineered vascular grafts", FASEB, 25(12):4253-63 (2011b).
Hibino, et al., "Tissue-engineered vascular grafts form neovessels that arise from regeneration of the adjacent blood vessel", FASB, 25(8):2731-9 (2011a).
Homann, et al., "Reconstruction of the RVOT with valved biological conduits: 25 years experience with allografts and xenografts", Eur. J. Cardiothorac. Surg., 17:624-30 (2000).
Information, CCL2 Vhemokine (C-C motif) ligand 2, http://www.ihop-net.org/UnPub/iHOP/gismo/92036.hmtl?Organism_ID=1, accessed Aug. 10, 2012.
Jay, et al., "Engineering of multifunctional gels integrating highly efficient growth factor delivery with endothelial cell transplantation", FASEB J., 22:2949-2956 (2008).
Jay, et al., "Nanoparticles containing anti-inflammatory agents as chemotherapy adjuvants: optimization and in vitro characterization", FASEB Jour., 10(1):133-40 (2008).
Jonas, et al., "Long-term follow-up of patients with synthetic right heart conduits", Circulation, 72(suppl II):II77-83 (1985).
Kakisis, et al., Artificial blood vessel: the Holy Grail of peripheral vascular surgery J. Vasc. Surg., 41:349-54 (2005).
Karamlou, et al., Oversizing pulmonary homograft conduits does not significantly decrease allograft failure in children, Eur. J. Cardiothorac. Surg., 27:548-53 (2005).
Kurobe, et al., "Comparison of the Biological Equivalence of Two Methods for Isolating Bone Marrow Mononuclear Cells for Fabricating Tissue-Engineered Vascular Grafts", Tissue Eng Part C, 21(6):597-604 (2015).
Langer and Vacanti, "Tissue engineering", Science, 260:920-6 (1993).
Lardo, et al., "Fluid dynamic comparison of intra-atrial and extracardiac total cavopulmonary connections", J. Thorac. Cardiovasc. Surg., 117:697-704 (1999).
Lee, et al., "TGF-β receptor 1 inhibition prevents stenosis of tissue-engineered vascular grafts by reducing host mononuclear phagocyte activation", FASB, 30:2627-36 (2016).
Levitsky, et al., Russian Congress of Interventional Cardioangiologists, Russia, Moscow, 1-11 (2005).
Lippincott, Remington's Pharmaceutical Sciences, 21st Ed.:889-964 (2005).
Mashkovsky, "Medications", Medicine, 12(2):404-407 (1993).
Mathiowitz and Langer, "Polyanhydride Microspheres as Drug carriers. I Hot—melt Microencapsulation", J. Controlled Release, 5:13-22 (1987).
Mathiowitz, et al., "Polyanhydride Microspheres as Drug Carriers: Microencapsulation by Solvent Removal", J. Appl. Polymer Sci., 35:755-774 (1988).
Mathiowitz, et al.," Novel Microcapsules for Delivery Systems", Reactive Polymers, 6:275-83 (1987).
Matsumura, et al., "Evaluation of tissue-engineered vascular autografts", Tissue Eng., 12:3075-83 (2006).
Matsumura, et al., "First evidence that bone marrow cells contribute to the construction of tissue-engineered vascular autografts in vivo", Circulation, 108(14):1729-34 (2003b).
Matsumura, et al., "Successful application of tissue engineered vascular autografts", Clinical experience, Biomaterials, 24:2303-8 (2003).
Mirensky, et al., "Tissue-engineered vascular grafts: does cell seeding matter?", Journal of Pediatric Surgery, 45(6):1299-1305 (2010).
Mizumoto, et al., "Enhanced contact hypersensitivity in human monocycle chemoattractant protein-1 transgenic mouse", Immunology, 204(4):477 (2001) Abstract only.
Naito, et al., "Successful clinical application of tissue-engineered graft for extracardiac Fontan operation", J. Thorac. Cardiovasc. Surg., 125:419-20 (2003).

(56) References Cited

OTHER PUBLICATIONS

Ovroutski, et al., "Comparison of somatic development and status of conduit after extracardiac Fontan operation in young and older children", Eur. J. Cardiothorac. Surg., 26:1073-9 (2004).

Owida, et al., "Artery vessel fabrication using the combined fused deposition modeling and electrospinning techniques", Rapid Prototyping Journal, 17(1):37 (2011).

Patterson, et al., "Tissue-engineered vascular grafts for use in the treatment of congenital heart disease: from the bench to the clinic and back again", Regenerative Medicine, 7(3):409-419 (2012).

Petrossian, et al., "Early results of the extracadiac conduit fontan operation", J. Thorac. Cardiovasc. Surg., 117:688-96 (1999).

Petrossian, et al., "The extracardiac conduit Fontan operation using minimal approach extracorporeal circulation: early and midterm outcomes", J. Thorac. Cardiovasc. Surg., 132:1054-63 (2006).

Poh, et al., "Blood vessels engineered from human cells", Lancet, 365:2122-24 (2005).

Roh, et al., "Construction of an autologous tissue-engineered venous conduit from bone marrow-derived vascular cells: optimization of cell harvest seeding techniques", Journal of Pediatric Surgery, 42(1):198-202 (2007).

Roh, et al., "Tissue-engineered vascular grafts transform into mature blood vessels via an inflammation-medicated process of vascular remodeling", PNAS, 107(10):4669-74 (2010).

Saito, et al., "A biodegradable polymer as a cytokine delivery system for inducing bone formationNature", Biotechnology, 19(4):332-335 (2001).

Samanek, "Children with congenital heart disease: probability of natural survival", Pediatr. Cardiol., 13:152-8 (1992).

Schiller, et al., "Participation of macrophages in atherosclerotic lesion morphology in LDLr-/- mice", Journal of Lipid Research, 45:1398-1409 (2004).

Shinoka, et al., "Midterm clinical result of tissue-engineered vascular autografts seeded with autologous bone marrow cells", J. Thorac. Cardiovasc. Surg., 129:1330-8 (2005).

Shinoka, et al., "Transplantation of a tissue-engineered pulmonary artery", New Engl. J. Med., 344(7):532-3 (2001).

Shinoka, et al., "Creation of viable pulmonary artery autografts through tissue engineering", J. Thorac. Cardiovasc. Surg., 115:536-46 (1998).

Solan, Age effects on vascular smooth muscle: an engineered tissue approach., Cell Transplant., 14(7):481-8 (2005).

Stacy, et al., "Targeted imaging of matrix metalloproteinase activity in the evaluation of remodeling tissue-engineered vascular grafts implanted in a growing lamb model", Journal of Thoracic and Cardiovascular Surgery, 148(5):2227-2233 (2014).

Stark, "The use of valved conduits in pediatric cardiac surgery", Peadiatr. Cardiol., 19:282-8 (1998).

Talacua, et al., "In Situ Tissue Engineering of Functional Small-Diameter Blood Vessels by Host Circulating Cells Only", Tissue Eng Pt A, 21(19-20):2583-94 (2015).

Watanabe, et al., "Tissue-engineered vascular autograft: inferior vena cava replacement in a dog model", Tissue Eng., 7(4):429-39 (2001).

Wolf, et al., "Antibodies against transforming growth factor-beta-1 suppress intimal hyperplasia in a rat model", Journal of Clinical Investigation, 93(3):1172-1178 (1994).

COMPOSITIONS AND METHODS FOR PROMOTING PATENCY OF VASCULAR GRAFTS

CROSS REFERENCE TO RELATED APPLICATIONS

This application is a continuation of U.S. application Ser. No. 15/850,364 filed on Dec. 21, 2017, which is a divisional of U.S. application Ser. No. 12/811,676 filed on Jul. 2, 2010, now U.S. Pat. No. 9,855,370, issued Jan. 2, 2018, which is a National Phase application under 35 U.S.C. § 371 of International Application No. PCT/US2009/030407 filed on Jan. 8, 2009, which claims priority to and benefit of U.S. Provisional Patent Application No. 61/010,406 filed on Jan. 8, 2008, by Christopher K. Breuer, Themis R. Kyriakides and Jason D. Roh, and where permissible are incorporated by reference in their entirety.

GOVERNMENT SUPPORT

This invention was made with government support under grant number 5K08HL083980 awarded by the National Institutes of Health. The government has certain rights in the invention.

FIELD OF THE INVENTION

This invention relates generally to compositions and methods for increasing the patency of vascular grafts, in particular vascular grafts made from biodegradable, polymeric scaffolds.

BACKGROUND OF THE INVENTION

Cardiac defects are the most common congenital anomalies affecting nearly 1% of all live births. Despite major advances in the treatment of congenital heart disease (CHD), it remains the leading cause of death due to congenital anomalies in the newborn period. CHD results from a myriad of structural anomalies that present over a broad spectrum. Single ventricle anomalies make up one of the largest groups of cardiac anomalies resulting in severe, life-threatening disease. Single ventricle anomalies are made up of a group of cardiac defects that are dramatically different from each other structurally, but share a common feature that only one of two ventricles is of adequate functional size. Some of the cardiac anomalies that result in single ventricle physiology include: tricuspid atresia, pulmonary atresia, and hypoplastic left heart syndrome. This group of congenital cardiovascular anomalies results in mixing of deoxygenated blood from the pulmonary circulation with oxygenated blood from the systemic circulation. The circulation of deoxygenated blood through the systemic circulation causes chronic hypoxia and cyanosis, a bluish discoloration of the skin resulting in the moniker "blue baby syndrome". Mixing of blood between the pulmonary and systemic circulation can also cause volume overload to the ventricle that if untreated can lead to heart failure. Untreated single ventricle cardiac anomalies are associated with 70% mortality during the first year of life (Samanek, *Pediatr. Cardiol.*, 13:152-8 (1992)). The treatment of choice for single ventricle anomaly is surgical reconstruction (Giannico, et al., *J. Amer. College Card*, 47(10):2065-73 (2006); Petrossian, et al., *J. Thorac. Cardiovasc. Surg.*, 132:1054-63 (2006)). Without surgery, survival into adulthood is unusual (Hager, et al., *J. Thorac. Cardiovasc. Surg.*, 123:1214-7 (2002)).

Despite the dramatic structural differences in the cardiac defects causing single ventricle physiology, the ultimate plans for staged surgical reconstruction are actually quite similar. The goal of this series of staged operations is to separate the pulmonary circulation from the systemic circulation. This eliminates the mixing of systemic and pulmonary blood flow, resulting in improved systemic oxygenation, and preventing volume overload, thus normalizing the volume work of the systemic ventricle, thereby preventing heart failure. This is accomplished through a series of staged operations designed to reconstruct the cardiovascular structures so that the single ventricle pumps oxygenated blood through the systemic circulation. The deoxygenated blood is then passively circulated through the pulmonary circulation where it is oxygenated and returned to the heart. This type of surgical procedure is referred to as a Fontan operation. The Fontan operation has undergone several modifications since it was first reported in 1971 (Fontan, et al., *Thorax*, 26(3):240-8 (1971)). The most commonly performed modification of the Fontan operation is the extra cardiac total cavopulmonary connection (EC TCPC). The modified Fontan operation is considered the standard of care for the treatment of patients with single ventricle cardiac anomalies and has substantially improved both the quality and long-term survival of these patients. However; it is still considered a palliative (non-curative) procedure with significant morbidity and mortality (Giannico, et al., *J. Amer. College Card.*, 47(10):2065-73 (2006); Petrossian, et al., *J. Thorac. Cardiovasc. Surg.*, 132:1054-63 (2006)). One important cause of morbidity and mortality in patients requiring the Fontan operation is the conduit used to connect the inferior vena cava to the right pulmonary artery when native tissue cannot be used (Jonas, et al., *J. Thorac. Cardiovasc. Surg.*, 117:688-96 (1999)). When Fontan and Kirklin reviewed the late outcome of an early cohort of patients surviving the Fontan procedure, they concluded that much of the late morbidity could be attributed to problems associated with conduit use (Fontan, et al, *Circulation*, 81:1520-36 (1990)). It is widely accepted that the ideal conduit has not yet been developed (Conte, *FASEB*, 12:43-5 (1998); Kakisis, *J. Vasc. Surg.*, 41:349-54 (2005)). Polytetrafluoro-ethylene (PTFE or Gore-Tex®) conduits are currently the most widely used vascular grafts for EC TCPC (Petrossian, et al., *J. Thorac. Cardiovasc. Surg.*, 132:1054-63 (2006)). Use of other synthetic conduits or even biological vascular grafts is described in the literature but to a much more limited extent compared to PTFE (Petrossian, et al., *J. Thorac. Cardiovasc. Surg.*, 117:688-96 (1999)).

While data describing the long-term graft failure rates for conduits used for EC TCPC is limited, long-term data regarding use of both valved and unvalved conduits for other similar congenital heart operations are widely available and are poor (Dearani, et al., *Ann. Thorac. Surg.*, 75:399-411 (2003)). Late problems include conduit degeneration with progressive obstruction, lack of growth potential, increased susceptibility to infection and increased risk for thromboembolic complications. Both synthetic and biological conduits are used for these operations. PTFE and other synthetic conduits such as Dacron lack growth potential, necessitating re-operation when a patient outgrows the vascular graft. Synthetic conduits are a significant cause of thrombo-embolic complication due to the large area of synthetic material in contact with blood, which causes activation of the coagulation cascade (Petrossian, et al., *J. Thorac. Cardiovasc.*

Surg., 117:688-96 (1999)). Other clinically available conduits including biological grafts such as homografts and hetero grafts are associated with significantly lower thromboembolic complication rates compared to synthetic grafts, however; they too lack growth potential and unfortunately have poor durability due to their propensity for accelerated calcific degradation and secondary graft failure (Stark, *Peadiatr. Cardiol.,* 19:282-8 (1998); Cleveland, et al., *Circulation,* 86(suppl II):II150-3 (1992); Jonas, et al., *Circulation,* 72(suppl II):II77-83 (1985)). These grafts tend to become stenotic and calcify. This process seems to be immune mediated and more aggressive in younger patients (Karamlou, et al., *Eur. J. Cardiothorac. Surg.,* 27:548-53 (2005)). It is basically assumed that all such conduits will eventually need to be replaced (Bermudez, et al., *Ann. Thorac. Surg.,* 77:881-8 (2004)). Re-operations are associated with significant morbidity and mortality with early post-operative mortality rates around 5% in the best centers (Dearani, et al., *Ann. Thorac. Surg.,* 75:399-411 (2003)). Early and midterm results for these grafts are variable with 5 year patency rates between 65-90%. Long-term data demonstrating graft failure rates between 70-100% at 10-15 years have been reported (Jonas, et al., *Circulation,* 72(suppl II):II77-83 (1985); *Peadiatr. Cardiol.,* 19:282-8 (1998); Homann, et al., *Eur. J. Cardiothorac. Surg.,* 17:624-30 (2000)). Primary determinants of graft failure include size (with an increased rate of failure in grafts less than 18 mm with another significant drop off below 15 mm) and re-operation (with primary grafts performing better than replacement grafts) (Homann, et al., *Eur. J. Cardiothorac. Surg.,* 17:624-30 (2000)). The best long-term results have been obtained when autologous tissue has been used for or incorporated into the conduit with long-term patency rates exceeding 80% (Bermudez, et al., *Ann. Thorac. Surg.,* 77:881-8 (2004)).

Autografts, conduits created from an individual's own (autologous) tissue, have better long-term effectiveness than any synthetic or biological conduit currently available for use in pediatric cardiovascular surgical applications (Dearani, et al., *Ann. Thorac. Surg.,* 75:399-411 (2003); Bermudez, et al., *Ann. Thorac. Surg.,* 77:881-8 (2004)). Unfortunately autografts are limited in supply, necessitating the use of synthetic or biological conduits in most cases (Homann, et al., *Eur. J Cardiothorac. Surg.,* 17:624-30 (2000)). Use of synthetic or biological vascular grafts result in increased graft failure rates and increased morbidity and mortality rates when compared to similar operations performed using autologous tissue (Jonas, et al., *Circulation,* 72(suppl II): II77-83 (1985); Bermudez, et al., *Ann. Thorac. Surg.,* 77:881-8 (2004)).

Complications arising from the use of currently available vascular grafts are a leading cause of postoperative morbidity and mortality after congenital heart surgery (Jonas, et al., *J. Thorac. Cardiovasc. Surg.,* 117:688-96 (1999)). Additionally the lack of growth potential of all currently available vascular conduits is problematic (Alexi-Meskishvili, et al., *Eur. J Cardiothorac. Surg.,* 18:690-5 (2000)). Use of over-sized grafts in an attempt to avoid outgrowing a conduit is widely practiced. Postponing surgery until the patient is between 2 and 4 years of age, when the diameter of the IVC approaches 60-80% of the adult frequently enables placement of near adult sized conduits (20-22 mm) and limits the need for conduit replacement based on somatic growth alone, however; graft over-sizing is associated with an increased risk of complications (Alexi-Meskishvili, et al., *Eur. J. Cardiothorac. Surg.,* 18:690-5 (2000)). Delaying surgery to minimize the number of re-operations can lead to cardiac dysfunction or even heart failure due to prolonged exposure to volume overload and chronic hypoxia (Petrossian, et al., *J. Thorac. Cardiovasc. Surg.,* 117:688-96 (1999)). Additionally, recent studies have demonstrated marked improvement in somatic growth in patients who undergo surgery at an earlier age, providing further support for the performance of EC TCPC at an earlier age (Ovroutski, et al., *Eur. J. Cardiothorac. Surg.,* 26:1073-9 (2004)). The upper limit of over-sizing is approximately 1.5 times the size of the native vessel after which point over-sizing will cause substantial negative hemodynamic consequences (Lardo, et al., *J. Thorac. Cardiovasc. Surg.,* 117:697-704 (1999)). Recent studies recommend limiting over-sizing conduits to 1.2 times the size of the native vessel because it is thought that the increased risk of thrombo-embolic complications associated with the use of over-sized grafts is greater than the risk of conduit replacement (Alexi-Meskishvili, et al., *Eur. J. Cardiothorac. Surg.,* 18:690-5 (2000)). The development of a vascular graft with growth potential would eliminate this problem and have dramatic implications for the field of congenital heart surgery.

Tissue engineering offers a strategy for constructing autologous grafts and thereby increasing the pool of potential autografts. Using the classical tissue engineering paradigm, autologous cells can be seeded onto a biodegradable tubular scaffold. The scaffold provides sites for cell attachment and space for neotissue formation (Langer and Vacanti, *Science,* 260:920-6 (1993)). The resulting neotissue can be used for reconstructive surgical applications such as creation of a vascular graft for use in pediatric cardiothoracic operations (Shinoka, et al., *J. Thorac. Cardiovasc. Surg.,* 115: 536-46 (1998)). Extensive large animal studies using both ovine and canine animal models, have demonstrated the feasibility of using tissue engineering methodology to construct conduits for use as large caliber grafts in the venous or pulmonary circulation (Shinoka, et al., *J. Thorac. Cardiovasc. Surg.,* 115:536-46 (1998); Watanabe, et al., *Tissue Eng.,* 7(4):429-39 (2001); Matsumura, et al., *Biomaterials,* 24:2303-8 (2003); Matsumura, et al., *Tissue Eng.,* 12:1-9 (2006)).

Many studies using biodegradable, synthetic scaffolds have employed vascular cells that were isolated from autologous vessel biopsies. More recent studies have explored the use of autologous cells obtained from bone marrow aspirate Matsumura, et al., *Biomaterials,* 24:2303-8 (2003)). Based in part on the success of animal studies and on the great promise associated with the development of a vascular graft with growth potential for congenital heart surgery, a pilot clinical study was conducted to evaluate the feasibility and safety of using tissue engineered vascular grafts as conduits for EC TCPC in patients with single ventricle cardiac anomalies (Shinoka, et al., *New Engl. J. Med.,* 344(7):532-3 (2001)); Naito, et al., *J. Thorac. Cardiovasc. Surg.,* 125: 419-20 (2003)). To date 25 TEVG have been implanted as conduits for EC TCPC with follow-up out through seven years (Shinoka, et al., *J. Thorac. Cardiovasc. Surg.,* 129: 1300-8 (2005)). The tissue engineered vascular grafts functioned well without evidence of graft failure. No graft has had to be replaced. There has been no graft related mortality. There have been two graft related complications, which include the development of significant stenosis in two small diameter (<18 mm) conduits. Both were successfully treated, the first with angioplasty and the second with angioplasty and stenting. There were no reported thromboembolic or hemorrhagic complications, infectious complication or evidence of aneurysm formation. Additionally serial imaging demonstrated the growth potential of these grafts. These data support the overall feasibility and safety of this technology.

The methodology of seeding synthetic vascular grafts with autologous cells, however, is still problematic for many reasons. First, it requires an invasive procedure (biopsy) in addition to the need for a substantial period of time in order to expand the cells in culture that limited its clinical utility. This approach also faces the inherent difficulty in obtaining healthy autologous cells from diseased donors (Poh, et al., Lancet, 365:2122-24 (2005); Solan, et al., Cell Transplant., 14(7):481-8 (2005)). The use of cell culture also results in an increased risk of contamination and even the potential for dedifferentiation of the cultured cells. The use of autologous cells to seed the polymeric grafts also limits the off-the-shelf availability of tissue engineered vascular grafts, thereby limiting their overall clinical utility.

Therefore, it is an object of the invention to provide methods for increasing the patency of biodegradable, synthetic vascular grafts without using cell seeding.

It is another object of the invention to provide biodegradable, synthetic vascular grafts with growth potential that have increased patency.

SUMMARY OF THE INVENTION

Methods for increasing the patency of biodegradable, synthetic vascular grafts are provided. The methods include administering one or more cytokines and/or chemokines that promote outward tissue remodeling of the vascular grafts and vascular neotissue formation. The polymeric vascular grafts are tubular, porous structures that allow for recruitment and integration of host cells into the graft that mediate remodeling and vascular neotissue formation. The vascular grafts are biodegradable, which allows for the grafts to be completely replaced by forming neotissue as they degrade. The methods do not require cell seeding of the vascular grafts, avoiding many problems associated with seeding, including the need for an invasive procedure to obtain autologous cells, the need for a substantial period of time in order to expand the cells in culture, the inherent difficulty in obtaining healthy autologous cells from diseased donors, and an increased risk of contamination and the potential for dedifferentiation of the cells. The disclosed biodegradable, synthetic vascular grafts therefore have a greater off-the-shelf availability and increased overall clinical utility.

The biodegradable, polymeric vascular grafts may be fabricated from biodegradable polymers using any known method. In one embodiment, the polymeric vascular grafts are fabricated from woven or non-woven sheets or felts or polymeric fibers. The polymers and fabrication methods are selected to produce vascular grafts with biomechanical properties, such as initial burst pressure, suture retention strength, elasticity and tensile strength, suitable for use as vascular conduits. Polymeric woven or non-woven sheets or felts may be further treated with polymeric sealants to modify the biomechanical properties of the graft and/or to control the total porosity and pore size distribution range of the vascular graft.

It is believed that cytokines and chemokines function to increase the patency of polymeric vascular grafts by causing the recruitment of host cells to the graft that promote vascular remodeling and vascular neotissue formation. Suitable cytokine and/or chemokines include those that promote the recruitment of host cells to the implanted polymeric vascular grafts. Particularly suitable cytokines and chemokines include those that promote early recruitment of monocytes to the implanted polymeric vascular grafts. Exemplary cytokines or chemokines include, but are not limited to, monocyte chemoattractant protein-1 (MCP-1), interleukin-1beta (IL-1β), and granulocyte colony stimulating factor (G-CSF or GCSF). Additional bioactive agents that promote adaptation of the vascular graft may also be administered.

Cytokines and/or chemokines may be administered in an effective amount to prevent, inhibit or reduce restenosis, thrombus or aneurysm formation in implanted polymeric vascular grafts. Cytokines and/or chemokines may be administered prior to vascular graft implantation, at the same time as vascular graft implantation, following vascular graft implantation, or any combination thereof. In one embodiment, cytokines or chemokines are administered either locally or systemically from a controlled release formulation.

In a preferred embodiment, cytokines or chemokines are administered locally at the site of graft implantation using a controlled release formulation. In one embodiment, the cytokine or chemokine is incorporated into or onto the polymeric vascular graft which functions as a controlled release formulation. The cytokine or chemokine may be dispersed evenly throughout the polymeric vascular graft using any known suitable method. In another embodiment, the cytokine or chemokine may be encapsulated in a second polymeric matrix that is incorporated into the polymeric vascular graft. In one embodiment, the cytokines or chemokines are encapsulated into microspheres, nanospheres, microparticles and/or microcapsules, and seeded into the porous vascular graft.

The biodegradable, synthetic vascular grafts may be used as venous, arterial or artero-venous conduits for any vascular or cardiovascular surgical application. Exemplary applications include, but are not limited to, congenital heart surgery, coronary artery bypass surgery, peripheral vascular surgery and angioaccess.

DETAILED DESCRIPTION OF THE INVENTION

I. Definitions

Figure 1:
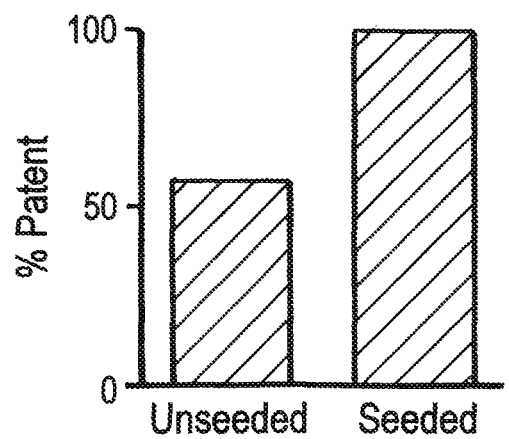
FIG. 1 is a bar graph showing the difference in patency rates (percent patent) between seeded and unseeded tissue engineered vascular grafts (TEVGs) at 24 weeks after implantation.

The terms "conduit", "graft", "vascular graft" and "scaffold" are used interchangeably herein.

"Restenosis", as defined herein, means a narrowing of the lumen of a blood vessel at a previously stenotic site (i.e., the site of balloon inflation during angioplasty), or narrowing of the lumen of a blood vessel or synthetic graft following an interventional procedure (e.g., narrowing of the venous side of an arterial-venous anastomosis following bypass surgery using a graft). Restenosis, as used herein, encompasses occlusion. Restenosis includes any luminal narrowing that occurs following an injury to the vessel wall. Injuries resulting in restenosis can therefore include trauma to an atherosclerotic lesion (as seen with angioplasty), a resection of a lesion (as seen with endarterectomy), an external trauma (e.g., a cross-clamping injury), or a surgical anastomosis.

"Copolymer" is used herein to refer to a single polymeric material that is comprised of two or more different monomers. The copolymer can be of any form, such as random, block, graft, etc. The copolymers can have any end-group, including capped or acid end groups.

"Biocompatible" as used herein refers to a material and any metabolites or degradation products thereof that are generally non-toxic to the recipient and do not cause any significant adverse effects to the subject.

"Biodegradable" refers to a material that will degrade or erode under physiologic conditions to smaller units or chemical species that are capable of being metabolized, eliminated, or excreted by the subject.

"Controlled release" or "modified release", as used herein, refers to a release profile in which the active agent release characteristics of time course and/or location are chosen to accomplish therapeutic or convenience objectives not offered by conventional dosage forms such as solutions, suspensions, or promptly dissolving dosage forms. Delayed release, extended release, and pulsatile release and their combinations are examples of modified release.

"Bioactive agent" or "active agent" is used herein to refer to therapeutic, prophylactic, and/or diagnostic agents. It includes without limitation physiologically or pharmacologically active substances that act locally or systemically in the body. A biologically active agent is a substance used for, for example, the treatment, prevention, diagnosis, cure, or mitigation of disease or disorder, a substance which affects the structure or function of the body, or pro-drugs, which become biologically active or more active after they have been placed in a predetermined physiological environment. Bioactive agents include biologically, physiologically, or pharmacologically active substances that act locally or systemically in the human or animal body. Examples can include, but are not limited to, small-molecule drugs, peptides, proteins, antibodies, sugars, polysaccharides, nucleotides, oligonucleotides, aptamers, siRNA, nucleic acids, and combinations thereof. "Bioactive agent" includes a single agent or a plurality of bioactive agents including, for example, combinations of two or more bioactive agents.

The terms "individual", "host", "subject", and "patient" are used interchangeably herein.

II. Methods for Promoting Patency of Biodegradable, Synthetic Vascular Grafts Patency of biodegradable, synthetic vascular grafts is increased by administering one or more cytokines and/or chemokines to promote long-term patency of biodegradable, synthetic vascular grafts. The administration of cytokines or chemokines increases the patency of the biodegradable, synthetic vascular grafts relative to the patency of the grafts in the absence of the cytokine or chemokine.

It is believed that cytokines and chemokines promote patency of biodegradable, synthetic vascular grafts by promoting the early recruitment of host cells, including monocytes, to the vascular graft that promote outward vascular tissue remodeling and vascular neotissue formation.

The disclosed biodegradable, synthetic vascular grafts do not require cell seeding to maintain patency of the grafts. This is advantageous, because it avoids problems associated with cell seeding, including the need for an invasive procedure to obtain autologous cells, the need for a substantial period of time in order to expand the cells in culture, the inherent difficulty in obtaining healthy autologous cells from diseased donors, and an increased risk of contamination and the potential for dedifferentiation of the cells. The disclosed biodegradable, synthetic vascular grafts therefore have a greater the off-the-shelf availability and increased overall clinical utility.

A. Polymeric Vascular Grafts

The polymeric vascular grafts disclosed herein are tubular porous conduits fabricated using biodegradable polymers. The pores in the polymeric vascular grafts allow for recruitment and integration of host cells into the graft. It is believed that recruited host cells mediate outward vascular tissue remodeling and vascular neotissue formation. Unlike synthetic vascular grafts that are currently in clinical use, the disclosed polymeric vascular grafts are biodegradable, which allows for the grafts to become replaced by forming neotissue as they degrade. Thus, the disclosed polymeric vascular grafts offer growth potential that is not possible with currently used synthetic vascular grafts.

The disclosed grafts are substantially tubular in shape with a round or substantially round cross section. The tubular grafts have a lumen extending throughout the length of the graft. The grafts may be of any appropriate length and diameter that is suitable for the intended surgical use of the graft. Typically, the graft should be slightly longer than the length of artery or vein that is to be replaced.

The porous polymeric vascular grafts may be fabricated using any appropriate method, such as melt processing, solvent processing, leaching, foaming, extrusion, injection molding, compression molding, blow molding, spray drying, extrusion coating, and spinning of fibers with subsequent processing into woven or non-woven constructs. Pores in the graft may be derived by any suitable method, including salt leaching, sublimation, solvent evaporation, spray drying, foaming, processing of the materials into fibers and subsequent processing into woven or non-woven devices. Preferably, the pores of the device are between 5 and 500 µm, more preferably between 5 and 250 µm, more preferably between 5 and 100 µm, in diameter.

In one embodiment, the grafts are formed from a felt or sheet like material of the polymer that can be formed into a tubular conduit. For example the device could be fabricated as a nonwoven, woven or knitted structure from extruded polymeric fibers. The polymeric sheet may be formed using any textile construction, including, but not limited to, weaves, knits, braids or filament windings. Any suitable method, such as electrospinning, may be used to fabricate the nonwoven or woven polymeric textile.

The polymers and fabrication methods selected to fabricate the polymeric vascular grafts are suitable to produce grafts with biomechanical properties suitable for use as vascular conduits. Biomechanical properties that are important for vascular graft function include initial burst pressure, suture retention strength and elasticity. In one embodiment, the initial burst pressure of the polymeric vascular graft is between about 1,500 mmHg and about 4,500 mmHg, preferably between about 2,000 mmHg and about 4,500 mmHg. In another embodiment, the polymeric vascular grafts possess suture retention strengths between about 1 N and about 5 N, preferably between about 2 N and about 4 N. In another embodiment, the intrinsic elasticity of the vascular grafts is between about 10 MPa and about 50 MPa, preferably between about 15 MPa and about 40 MPa. In another embodiment, the initial tensile strength of the vascular grafts is between about 1 MPa and about 10 MPa, preferably between about 3 MPa and about 6 MPa.

1. Biodegradable Polymers

The biodegradable, synthetic vascular grafts may be fabricated using any known biodegradable polymer, co-polymer, or mixture thereof. Many suitable biodegradable polymers are known in art.

Examples of preferred biodegradable polymers include synthetic polymers that degrade by hydrolysis such as poly(hydroxy acids), such as polymers and copolymers of lactic acid and glycolic acid, polyanhydrides, poly(ortho) esters, polyesters, polyurethanes, poly(butic acid), poly(valeric acid), poly(caprolactone), poly(hydroxyalkanoates), and poly(lactide-co-caprolactone). The foregoing materials may be used alone, as physical mixtures (blends), or as co-polymers.

In a preferred embodiment, the biodegradable, synthetic vascular grafts are fabricated from polyglycolic acid or poly-L-lactic acid. The examples below demonstrate that these biodegradable polymers can be extruded into fibers and fabricated into nonwoven felts to produce vascular grafts with biomechanical properties suitable for use as vascular conduits, such as tensile strength, elastic modulus and suture retention strength when combined with appropriate polymeric sealants. These vascular grafts also possess good in vivo biocompatibility and functionality.

2. Sealants

Synthetic vascular grafts fabricated from nonwoven, woven or knitted sheets or felts of biodegradable polymers may be further treated with polymeric sealants. The polymeric sealants function to modify the biomechanical properties of the vascular grafts, such as tensile strength and elasticity. Polymeric sealants may also be used to control the total porosity and pore size distribution range of the vascular graft.

Polymeric sealants for the disclosed biodegradable synthetic vascular grafts may be any biodegradable polymer, including, but not limited to, the list of biodegradable polymers listed above. In one embodiment, the polymeric sealant is a copolymer of poly(ε-caprolactone) and poly(L-lactide).

Polymeric sealants may be added to tubular synthetic grafts dissolved in an appropriate solvent to allow for the sealant to penetrate the nonwoven, woven or knitted sheet or felt of biodegradable polymers feinting the graft. The polymeric sealant may then be quickly transformed from liquid to solid phase by lowering the temperature of the graft. Solvents may then be removed by an appropriate technique, such as lyophilization.

B. Cytokines and Chemokines

Suitable cytokines and chemokines include cytokines and chemokines that promote the recruitment of host cells to implanted synthetic vascular grafts. Particularly suitable cytokines and chemokines include those that promote early recruitment of monocytes to implanted synthetic vascular grafts following implantation. It is believed that monocytes that are recruited early to vascular grafts promote outward vascular tissue remodeling and vascular neotissue formation.

Exemplary cytokines and chemokines include, but are not limited to, interleukin (IL) 1α, IL-1β, IL-2, IL-3, IL-4, IL-5, IL-6, IL-7, IL-9, IL-10, IL-12(p40), IL-12(p70), IL-13, IL-15, IL-17, IP-10, eotaxin, interferon γ (IFNγ), granulocyte colony-stimulating factor (G-CSF), granulocyte/macrophage colony-stimulating factor (GM-CSF), monocyte chemoattractant protein 1 (MCP-1), macrophage inflammatory protein 1α (MIP-1α), RANTES, tumor necrosis factor (TNF)-α, platelet-derived growth factor (PDGF)-AA, PDGF-AB/BB, TGF-beta and VEGF, or combinations thereof. In one embodiment, the cytokine or chemokine is G-CSF. In another embodiment, the cytokine or chemokine is MCP-1. In another embodiment, the cytokine or chemokine is IL-1β.

The examples below demonstrate that human bone marrow cells (hBMCs), which promote patency when seeded onto synthetic vascular scaffolds, significantly increase production and secretion of MCP-1 and IL-1β when seeded onto polymeric scaffolds. The examples also demonstrate that polymeric vascular grafts seeded with bone marrow cells from MCP-1−/− mice have decreased internal lumen diameters and significantly increased graft wall thickness when implanted into mice as compared to polymeric vascular grafts seeded with bone marrow cells from wild-type mice. The examples also demonstrate that administration of G-CSF prior to implantation of polymeric vascular scaffolds significantly increases the patency of the vascular scaffold.

C. Additional Bioactive Agents

Additional bioactive agents that promote vascular graft adaptation may also be administered. Suitable bioactive agents or drugs include, but are not limited to: anti-thrombogenic agents such as heparin, heparin derivatives, urokinase, and PPack (dextrophenylalanine proline arginine chloromethylketone; anti-proliferative agents such as enoxaparin, angiopeptin, or monoclonal antibodies capable of blocking smooth muscle cell proliferation, hirudin, and acetylsalicylic acid; antineoplastic/antiproliferative/anti-mitotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vasoactive mechanisms.

D. Pharmaceutical Compositions and Methods of Administration

Cytokines or chemokines are administered to a subject receiving a polymeric vascular graft in an effective amount to prevent, inhibit or reduce restenosis, thrombus or aneurysm formation in implanted vascular grafts. The precise dosage will vary according to a variety of factors such as the nature of the particular cytokine(s) or chemokine(s) being administered, the route of administration, and subject-dependent variables (e.g., age, etc.).

Cytokines or chemokines may be administered systemically or locally at the site of vascular graft implantation. Cytokines or chemokines may be administered prior to vascular graft implantation, at the same time as vascular graft implantation, following vascular graft implantation, or any combination thereof. In one embodiment, cytokines or chemokines are administered either locally or systemically from a controlled release formulation. The cytokines or chemokines may be administered separately from additional bioactive agents or may be co-administered.

Pharmaceutical compositions containing peptides or polypeptides (i.e. cytokines and chemokines) may be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration. The compositions can be formulated in dosage forms appropriate for each route of administration. Compositions containing bioactive agents that are not peptides or polypeptides can additionally be formulated for enteral administration.

In one embodiment, the cytokine or chemokine is incorporated into or onto the vascular graft. The cytokine or chemokine may be dispersed evenly throughout the polymeric vascular graft using any known suitable method. The cytokine or chemokine may be incorporated directly into the vascular graft or may be encapsulated in the form of microspheres, nanospheres, microparticles and/or microcapsules, and seeded into the porous vascular graft.

1. Formulations for Parenteral Administration

In one embodiment, polypeptide bioactive agents, including cytokines and chemokines, are administered in an aqueous solution by parenteral injection. The formulation may also be in the form of a suspension or emulsion. In general, pharmaceutical compositions are provided including effective amounts of a cytokine or chemokine, and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80, Polysorbate 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Topical Administration

In another embodiment, bioactive agents, including cytokines or chemokines, are administered topically.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder inhalers.

Formulations for administration to the mucosa will typically be spray dried drug particles, which may be incorporated into a tablet, gel, capsule, suspension or emulsion. Standard pharmaceutical excipients are available from any formulator. Oral formulations may be in the form of chewing gum, gel strips, tablets or lozenges.

Transdermal formulations may also be prepared. These will typically be ointments, lotions, sprays, or patches, all of which can be prepared using standard technology. Transdermal formulations will require the inclusion of penetration enhancers.

3. Controlled Delivery Polymeric Matrices

In one embodiment, cytokines or chemokines may be administered systemically or locally using controlled release formulations. In a preferred embodiment, cytokines or chemokines are administered locally at the site of graft implantation using a controlled release formulation. In one embodiment, the cytokine or chemokine is incorporated into or onto the polymeric vascular graft which functions as a controlled release formulation. The cytokine or chemokine may be dispersed evenly throughout the polymeric vascular graft using any known suitable method. For example, one or more cytokines or chemokines may be added to the polymeric scaffold during fabrication by adding them to the polymer solution or emulsion or during the fabrication of a polymeric textile, such as by an electrospinning process. Additionally, or alternatively, one or more cytokines or chemokines may be added to the polymeric graft following fabrication. In another embodiment, the cytokine or chemokine is preferentially localized to either the exterior or the lumen of the tubular polymeric vascular graft.

In another embodiment, the cytokine or chemokine may be encapsulated in a second polymeric matrix that is incorporated into the polymeric vascular graft. In one embodiment, the cytokines or chemokines are encapsulated into microspheres, nanospheres, microparticles and/or microcapsules, and seeded into the porous vascular graft. The matrix can be in the form of microparticles such as microspheres, where polypeptides are dispersed within a solid polymeric matrix or microcapsules, where the core is of a different material than the polymeric shell, and the polypeptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel, and used as a coating for the vascular graft.

Either non-biodegradable or biodegradable matrices can be used for delivery of cytokines or chemokines, although biodegradable matrices are preferred. These may be natural or synthetic polymers, although synthetic polymers are preferred due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release*, 5:13-22 (1987); Mathiowitz, et al., *Reactive Polymers*, 6:275-283 (1987); and Mathiowitz, et al., *J. Appl. Polymer Sci.*, 35:755-774 (1988).

4. Formulations for Enteral Administration

Bioactive agents that are not peptides or polypeptides can also be formulated for oral delivery. Oral solid dosage forms are known to those skilled in the art. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in viva clearance of the present proteins and derivatives. See, e.g., Remington's Pharmaceutical Sciences, 21st Ed. (2005, Lippincott, Williams & Wilins, Baltimore, Md. 21201) pages 889-964. The compositions may be prepared in liquid form, or may be in dried powder (e.g., lyophilized) form. Liposomal or polymeric encapsulation may be used to formulate the compositions. See also Marshall, K. In: Modern Pharmaceutics Edited by G. S. Banker and C. T. Rhodes Chapter 10, 1979. In general, the formulation will include the active agent and inert ingredients which protect peptide in the stomach environment, and release of the biologically active material in the intestine.

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

Controlled release oral formulations may be desirable. Non-polypeptide bioactive agents can be incorporated into an inert matrix which permits release by either diffusion or leaching mechanisms, e.g., films or gums. Slowly disintegrating matrices may also be incorporated into the formulation. Another form of a controlled release is one in which the drug is enclosed in a semipermeable membrane which allows water to enter and push drug out through a single small opening due to osmotic effects. For oral formulations, the location of release may be the stomach, the small intestine (the duodenum, the jejunem, or the ileum), or the large intestine. Preferably, the release will avoid the deleterious effects of the stomach environment, either by protection of the active agent (or derivative) or by release of the active agent beyond the stomach environment, such as in the intestine. To ensure full gastric resistance an enteric coating (i.e, impermeable to at least pH 5.0) is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films or as capsules such as those available from Banner Pharmacaps.

III. Uses for Biodegradable, Synthetic Vascular Grafts with Increased Patency

The biodegradable, synthetic vascular grafts disclosed herein may be used as venous, arterial or artero-venous conduits for any vascular or cardiovascular surgical application. Exemplary applications include, but are not limited to, congenital heart surgery, coronary artery bypass surgery, peripheral vascular surgery and angioaccess.

Vascular bypass grafting is most commonly performed for the treatment of vessel stenosis. However, vascular grafts are also used for the treatment of other conditions such as arterial aneurysm or chronic renal failure (as access for hemodialysis). Vascular grafting can be performed by conventional surgery or endovascular techniques.

Coronary artery bypass grafting (CABG) is one example of vascular bypass surgery. With this procedure, a bypass graft is used to bypass the coronary artery distal to the site of stenosis or occlusion. When a vein graft is used, one end is anastomosed to the aorta and the other end is anastomosed to the coronary artery beyond the stenosis or occlusion. When an arterial graft is used, the proximal end is left undisturbed (thus preserving the artery's normal blood inflow) and the distal end is anastomosed to the coronary artery beyond the stenosis or occlusion.

Typically, an anastomosis (i.e., the surgical union of tubular parts) between the in situ artery or vein and the synthetic graft is created by sewing the graft to the in situ vessel with suture. Commonly used suture materials include proline (extruded polypyline) and ePTFE.

EXAMPLES

Example 1. Seeded Human Bone Marrow Mononuclear Cells (hBMCs) Improve the Functional Outcome and Vascular Development of TEVG Materials and Methods:
Biodegradable PGA-P (CL/LA) Scaffold Construction A dual cylinder chamber molding system was constructed from a 6.5 mm diameter polypropylene rod. A 1.4 mm diameter inner cylinder was cored through the center of the rod for a length of 30 mm and gradually tapered out to 6.0 mm at the inlet. Polyglycolic acid (PGA) nonwoven felt (ConcordiaFibers, Coventry, RI) was used for the framework of the scaffold. Felts were 300 mm thick with approximately 90% (PGA) or 83% (PLLA) total porosity. The gradual taper of the inner cylinder enabled flat felt sections (6.0 mm×4.0 mm) to be easily shaped into tubes during their insertion through the inlet of the dual cylinder chamber system. Stainless steel needles (21 g) were then introduced into the opposing end to maintain the inner lumen and further compress the felt. A 50:50 copolymer sealant solution of 3-caprolactone and L-lactide (P(CL/LA)) (263,800 Da, Absorbable Polymers International, Birmingham, AL) was created by dissolving the copolymer at 5% (w/v) in 1,4-dioxane. The P(CL/LA) sealant was injected into the inlet of the chamber system and allowed to penetrate the felt and fuse the open seam. The hybrid polyester scaffolds were snap-frozen at −20° C. for 30 minutes to enable rapid transformation of the P(CL/LA) sealant from liquid to solid phase, creating a sealed tube with a newly defined porous structure of P(CL/LA) polymer interconnecting the PGA fibers. The scaffolds were lyophilized for 24 hours to eliminate the solvents before removing them from the dual cylinder chamber system.

BMC Isolation

Murine bone marrow was isolated from the femur bones of MCP-1−/− or syngeneic C57BL/6 mice (Jackson Laboratories). Unfractionated human bone marrow (10 donors) was purchased from Lanza. Bone marrow was diluted 1:1 in sterile PBS and filtered through a 100 pin nylon mesh. Mononuclear cells were then isolated by density gradient centrifugation using histopaque-1077 (human) or histopaque-1068 (mouse) (Sigma).

BMC Seeding onto PGA-P(CL/LA) Scaffolds

A fibrin gel solution was used to attach BMC to the scaffold. BMC were suspended at $2\times10^6$ cells/ml in sterile fibrinogen solution (100 mg/ml human fibrinogen [Sigma] in PBS). Fifty microliters of BMC-fibrinogen solution ($1\times10^6$ BMC) was statically seeded onto each scaffold. The cell solution was solidified onto the scaffold by adding sterile thrombin solution (100 U/ml human thrombin [Sigma] in 40 mM $CaCl_2$ in PBS). Seeded scaffolds were incubated at 37° C. in RPMI-1640 medium with 10% FBS until ready to be surgically implanted. All scaffolds were implanted within 48 hours of seeding.

Infrarenal IVC Interposition Surgery

All scaffolds were sutured into the infrarenal inferior vena cava (IVC) of 3-4 month old, female C.B-17 SCID/bg mice (Taconic Farms). Anesthetized mice were placed in the supine position and opened with an abdominal midline incision. Infrarenal IVC or aorta was exposed under 5× magnification, cross-clamped, and excised. Three millimeter length scaffolds were then inserted as interposition grafts using a running 10-0 nylon suture for the end-to-end proximal and distal anastomoses. Animals were recovered from surgery and maintained without the use of any anticoagulation or antiplatelet therapy. A total of 97 animals were implanted with BMC-seeded, unseeded, or MCP-1 eluting scaffolds. At 1 d, 3 d, 1 wk, 3 wk, 6 wk, 10 wk, and 24 wk, animals were sacrificed and grafts underwent in-vivo perfusion fixation under conditions of physiological pressure prior to explanation. All animal experiments were done in accordance with the institutional guidelines for the use and care of animals, and the institutional review board approved the experimental procedures described.

Micro-Computed Tomography Angiography (microCTA)

In vivo patency and morphology of the TEVG were evaluated using microCTA. Anesthetized mice were anticoagulated with 100 IU heparin prior to sacrifice. A PE-10 (polyethylene) catheter was inserted into either the IVC or aorta and 300 ml of Omnipaque (300 mg/ml) was injected into the respective venous or arterial circulatory system. Mice were then imaged in an X-O™ microCT (Gamma-Medica, Northridge, CA). Three-dimensional reconstruction was done using COBRA software (Exxim Computing Corporation). Images were combined using Total Commander (Ghisler & Co.) and volume rendered with AMIDE imaging software (Loening).

Histology

Explanted grafts were fixed in 10% formalin overnight and then embedded in paraffin. Sections were stained with H&E, Gamori trichrome (collagen), and Verhoeff-van Gieson (elastin). Using previously published methods; some pre-implant hBMC-seeded scaffolds were embedded in glycolmethacrylate to maintain better histologic structure with processing.

Morphometric Analysis

Internal diameter and wall thickness were measured for each explanted scaffold using ImageJ software (NIH).

Statistical Analysis

All data are presented as mean±SEM. Statistical significance was calculated in MS Excel and SPSS 11.5 for Windows. In all multi-group analysis overall comparisons between groups were performed with the one-way ANOVA. If a significant difference was found, pair-wise comparisons were carried out using the Tukey's test, correcting for multiple pair-wise analysis. For strictly pair-wise comparisons, independent student's t-test was carried out. Probability values less than 0.05 were regarded as significant.

Results:

Seeding hBMC onto scaffolds significantly improved their patency rates as WC interposition grafts compared to unseeded scaffolds implanted in parallel. By post-operative week 10, three out of seven unseeded scaffolds were fully occluded, one was >70% stenosed, and the remaining three were patent (FIG. 1). Micro-CT angiography showed that mice compensated for graft obstruction by developing large venous collaterals, suggesting that occlusion was likely due to a gradual stenotic process rather than an acute thrombotic event. Confirmatory histological analysis of occluded scaffolds showed obstructive cellular in-growth into the lumen. Conversely, when hBMC seeding was performed prior to implantation, 100% patency rates were obtained (FIG. 1). All hBMC-seeded scaffolds (n=5) were patent at 10 weeks with well-defined internal lumens as determined by both micro-CT angiography and histological analysis.

To ensure that hBMC seeding did not merely delay lumen occlusion, three hBMC-seeded scaffolds were followed for 24 weeks to evaluate long-term vascular development and function. All three seeded TEVG remained patent, and morphologically and histologically resembled native mouse IVC. The graft wall thickness substantially decreased, leaving an inner lumen and vessel wall comparable to that of native IVC. The original scaffold material degraded, and had been effectively replaced by a mature neovessel with an organized vascular architecture. A clearly defined intima, consisting of a confluent endothelial monolayer, and media, containing 1-2 layers of smooth muscles cells, were present. Circumferentially oriented collagen fibrils made up the supportive adventitial layer.

Example 2. Stem Cells Constitute a Minor Fraction of Seeded hBMCs

Materials and Methods:

Materials and methods were as described in Example 1 except as described below.

Characterization of hBMCs

Flow cytometry was used to identify and quantify subpopulations in the mononuclear cell fraction of human bone marrow. Human BMC from five different donors were used and tested in triplicate. Antibodies used were purchased from BD Biosciences CD8 PerCP (SK1), CD14 FITC (M5E2), CD31 FITC (WM59), CD34 PE and PerCP-Cy5.5 (8G12), CD45 APC-Cy7 (2D1), CD56 PE (NCAM16.2), CD146 (P1H12), CD73 PE (AD2), CD90 FITC (5E10), 7AAD; E-Bioscience CD3 APC (HIT3a), CD4 FITC (L3T4), CD19 (PE-Cy7); Miltenyi Biotec CD133 APC (AC133); R&D Systems VEGFR2 PE (89106); and AbD Serotec CD105 Alexa 647 (SN6). Cells were acquired on a FACSAria cell sorter and results analyzed using DIVA software (BD Bioscience).

Quantitative Image Analysis

Relative cellularity was measured for each explanted scaffold. Two separate sections of each explant were stained with H&E and imaged at 400× magnification, noted as a high power field (hpf). The number of nuclei was then counted in five regions of each section and averaged. Host mouse monocytes and seeded human BM-MNG subpopulations were identified by positive F4/80, hCD45, hCD34 and hCD31 expression respectively, were also quantified in pre-implant scaffolds and in post-operative week 1 explants, using similar methods.

Results:

To determine the mechanism by which seeded hBMC improved vascular growth and development of TEVG, the phenotypes and relative abundances of cell populations within the human BMC population used for seeding were first examined. Human BMC consisted mainly of mature leukocyte populations, including monocytes (1014.7%), $CD4^+$ T cells (7.0±2.7%), $CD8^+$ T cells (7.9±2.5%), B cells (6.4±2.1%), and NK cells (3.2±1.4) (Table 1).

TABLE 1

Summary of FACS analysis of human BM-MNC

| Cell Type | Staining Panel | Percent BMC |
|---|---|---|
| Late-outgrowth EPC | (+) AC133, VEGF-R2<br>(−) CD45 | 0.0029 ± 0.0042 |
| Early-outgrowth EPC | (+) CD14, VEGF-R2 | 1.7 ± 1.2 |
| Mature endothelial cell | (+) CD31, CD146<br>(−) CD45 | 0.0050 ± 0.024 |
| Mesenchymal stem cell | (+) CD90, CD73, CD105<br>(−) CD45, CD34 | 0.0013 ± 0.00096 |
| Hematopoietic stem cell | (+) CD34 | 1.8 ± 0.53 |
| Monocyte | (+) CD45, CD14 | 10 ± 4.7 |
| CD4 T cell | (+) CD3, CD4 | 7.0 ± 2.7 |
| CD8 T cell | (+) CD3, CD8 | 7.9 ± 2.5 |
| B cell | (+) CD19 | 6.4 ± 2.1 |
| Natural killer cell | (+) CD56 | 3.2 ± 1.4 |
| Other (neutrophils, erythroblasts, etc.) | | 56 ± 10 |

The largest population of adult stems cells identified was $CD34^+$ hematopoietic stem cells (HSC; 1.8±0.53%). $AC133^+KDR^+CD45^-$ cells, likely to be late-outgrowth endothelial progenitor cells (L-EPC), made up 0.0029±0.0042% of the BMC population, while $CD90^+CD73^+CD105^+CD45^-CD34^-$ mesenchymal stem cells (MSC) constituted the smallest percentage of BMC, with yields of only 0.0013±0.00096%. The relative paucity of progenitor cells, smooth muscle cells, and endothelial cells present in the BMC first raised the possibility that the seeded BMC may not be the source of the cellular constituents of vascular neotissue.

Static seeding, consisting of direct pipetting of a concentrated suspension of hBMC into scaffolds resulted in a similar distribution of cell types as in the original population, i.e., there was no obvious preference for any particular sub-population. Prior to implantation, the majority of hBMC in the scaffold were $CD45^+$ mature leukocytes, with greater than 30 cells per high power field (hpf). $CD31^+$ mature EC and $CD34^+$ stem cells were also identified, but in much lower numbers, with fewer than 1 cell per hpf respectively. No alpha-smooth muscle actin (αSMA) expression was detectable prior to implantation.

Example 3. Seeded hBMCs are not Incorporated into the Developing Neovessel

Materials and Methods:

Materials and methods were as described in Examples 1 and 2 except as described below.

Immunohistochemistry

Species-specific antibodies were used to distinguish between seeded human cells and recruited murine host cells. Human-specific primary antibodies used included mouse-anti-human CD31 (Dako), CD68 (Dako), CD34 (Abeam), and CD45 (AbD Serotec). Mouse-specific primary antibodies used included rat-anti-mouse Mac-3 (BD Bioscience), F4/80 (AbD Serotec), IL-1beta (R&D Systems), and goat-anti-mouse VEGF-R2 (R&D Systems, minimal cross-reactivity). Primary antibodies that cross-reacted with both species were mouse-anti-human α-smooth muscle actin (αSMA) (Dako), VEGF (Santa Cruz), and rabbit-anti-human von Willebrand Factor (vWF) (Dako). Antibody binding was detected using appropriate biotinylated secondary antibodies, followed by binding of streptavidin-HRP and color development with 3,3-diaminobenzidine (Vector). Nuclei were then counterstained with hematoxylin. For immunofluorescence detection, a goat-anti-rabbit IgG-Alexa Fluor 568 (Invitrogen) or a goat-anti-mouse IgG-Alexa Fluor 488 (Invitrogen) was used with subsequent 4',6-diamidino-2-phenylindole (DAPI) nuclear counterstaining.

Detection of Human RNA in TEVG

TEVG harvested 1, 3, 7, or 21 days after implantation or immediately prior to implantation were snap-frozen in liquid nitrogen, and RNA was extracted by mechanical crushing over dry ice followed by incubation in RLT lysis buffer (Oiagen). Samples were passed through Qiashredder columns (Oiagen) and processed using RNeasy mini kits (Oigen) according to the manufacturer's protocol. Reverse transcription with random hexamer and oligo-dT primers was performed according to the Multiscribe RT system protocol (Applied Biosystems). PCR reactions were prepared with TaqMan 2×PCR Master Mix and pre-developed assay reagents from. Applied Biosystems (human GAPDH, Hs99999905 ml. mouse HPRT, Mm00446968 ml) and analyzed on an iQ5 (Bio-Rad). Species-specificity of the human and mouse probes was confirmed on human and mouse control artery segments. To determine the limits of detection of human RNA, standard curves were generated by measuring human GAPDH levels obtained from 10-fold serial dilutions of human BMC cells in culture and human BMC cells seeded onto scaffolds. The limit of detection of this assay was between 10 and 100 cells.

Figure 2:
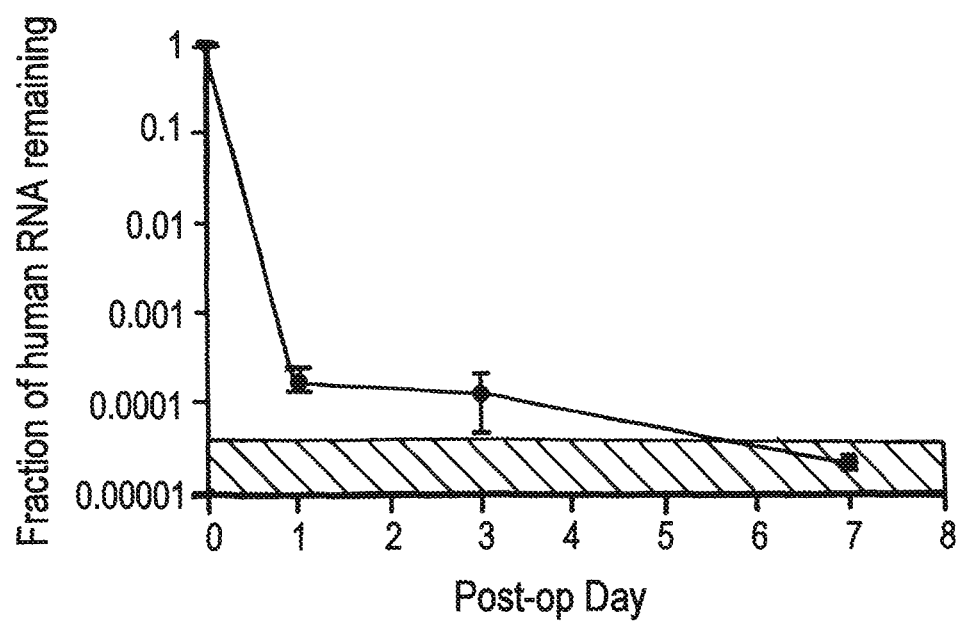
FIG. 2 is a line graph showing the fraction of human RNA (GAPDH) remaining in the TEVG as a function of days following graft implantation. RNA quantitation was performed using Q-RT-PCR. The hatched area represents the Q-RT-PCR limit of detection.

Results:

To determine if seeded hBMC or their progeny were directly contributing to the cellularity of the developing TEVG, these cells were next tracked over 24 weeks using human-specific markers and immunohistochemistry. $CD34^+$ human stem cells could no longer be detected by post-operative week 1, but $CD68^+$ human monocytes and $CD31^+$ human EC could still be detected within the scaffold wall. Neither cell type, however, was identified along the luminal surface, the location of vascular neotissue formation. By 3 weeks, no human cells expressing CD45, CD68, CD31, or CD34 could be detected anywhere in the grafts, suggesting that seeded hBMC were not likely present after this time point. Human specific GAPDH RNA detection via Q-RT-PCR confirmed the presence of human RNA on the TEVG prior to implantation and failed to detect any human RNA after the 7 POD (FIG. 2).

Figure 3:
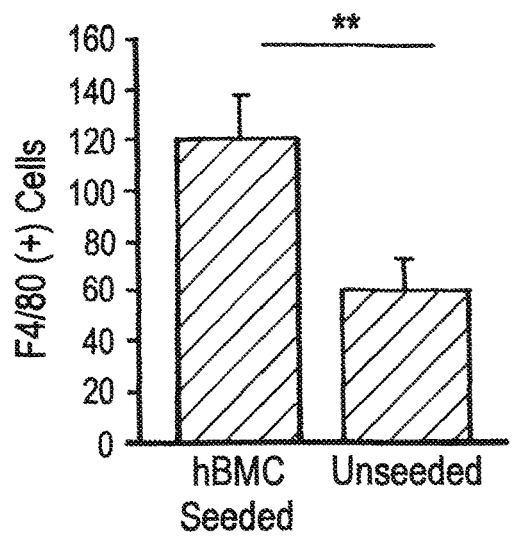
FIG. 3 is a bar graph showing the number of F4/80 positive mouse monocytes/macrophages per cell-seeded (human bone marrow cell (hBMC)) or unseeded scaffold at week 1 following scaffold implantation.

Although seeded hBMC were not permanently incorporated into the developing neovessel, they did affect the cellular development of the scaffold. Total cellularity of both hBMC-seeded and unseeded scaffolds progressively increased over 10 weeks, with the most substantial change occurring during the first week of development. At postoperative days 1 and 3, no significant differences in cellularity could be detected between hBMC-seeded scaffolds and unseeded scaffolds. However, by day 7, the increase in cellularity was significantly greater for hBMC-seeded scaffolds (n=6; 270±22 cells/hpf) compared to unseeded scaffolds (n=6; 160±40 cells/hpf) (p<0.001). This increased cellularity was primarily due to a significantly increased infiltration of host mouse monocytes into hBMC-seeded scaffolds (120±20 monocytes/hpf), as compared to unseeded scaffolds (60±12 monocytes/hpf) (p<0.001) (FIG. 3).

Example 4. BMC-Derived MCP-1 is a Critical Molecule in TEVG Development

Materials and Methods

Materials and methods were as described in Examples 1-3 except as described below.

ELISA for Cytokine and Chemokine Profile hBMC were cultured at $2\times10^6$ cells/ml on either PGA-P(CL/LA) scaffold or tissue culture plastic for 48 hrs in RPMI-1640+10% FBS. VEGF, SDF-1, IL-1β, and MCP-1 levels in the supernatants were measured using ELISA kits from R&D Systems. Minimum detection values were SDF-1 alpha 156 pg/mL, VEGF 15.6 pg/mL, IL-1beta 19 pg/mL and MCP-1 31.2 pg/mL.

Figure 4A:
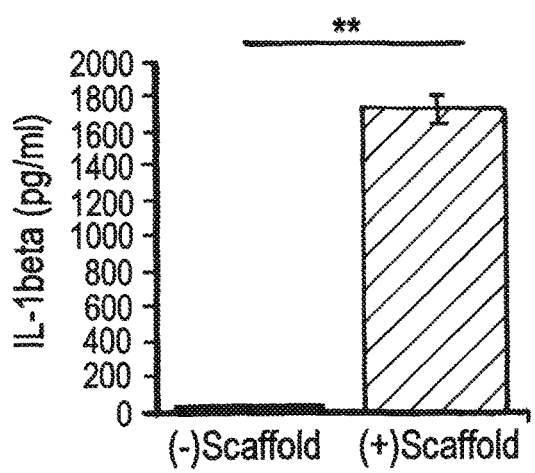
FIG. 4A is a bar graph showing the concentration (pg/ml) of IL-1beta produced by hBMCs when seeded onto scaffolds or unseeded, as determined by ELISA.
Figure 4B:
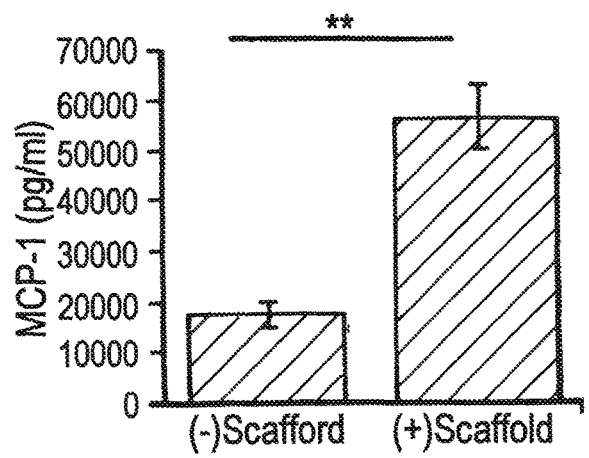
FIG. 4B is a bar graph showing the concentration (pg/ml) of MCP-1 produced by hBMCs when seeded onto scaffolds or unseeded, as determined by ELISA.

Results:

Based on the above findings, it was hypothesized that host monocytes promoted neovessel development. The remaining examples address how seeded hBMC could increase early host monocyte recruitment. It was first examined how interactions with scaffold biomaterials affected production of chemotactic factors by hBMC. ELISA was used to test for the presence of several candidate chemokines including: interleukin-1beta (IL-1β), MCP-1, stromal derived factor-1alpha (SDF-1α) and vascular endothelial growth factor (VEGF). Exposure to scaffold was found to significantly increase the amount of interleukin-1beta (IL-1β) and MCP-1 secreted by hBMC (FIGS. 4A and 4B). The production of stromal derived factor-1alpha (SDF-1α) and vascular endothelial growth factor (VEGF), two factors frequently associated with stem cell recruitment, either with or without exposure to scaffold material was below the level of detection of the ELISA.

Figure 5A:
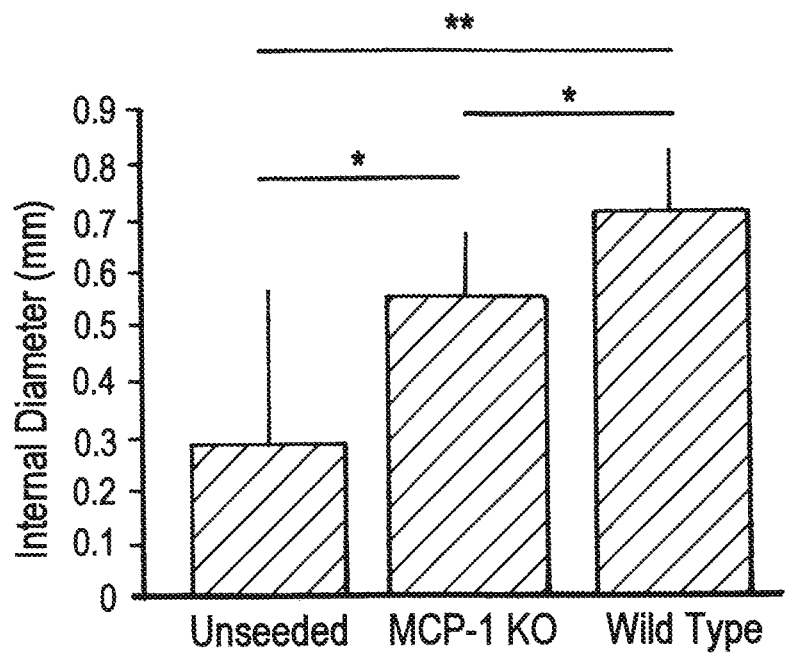
FIG. 5A is a bar graph showing the internal diameter (mm) of TEVGs at 10 weeks after implantation. TEVGs were unseeded, seeded with BMCs from wild-type mice, or seeded with cells from MCP-1 knockout mice.
Figure 5B:
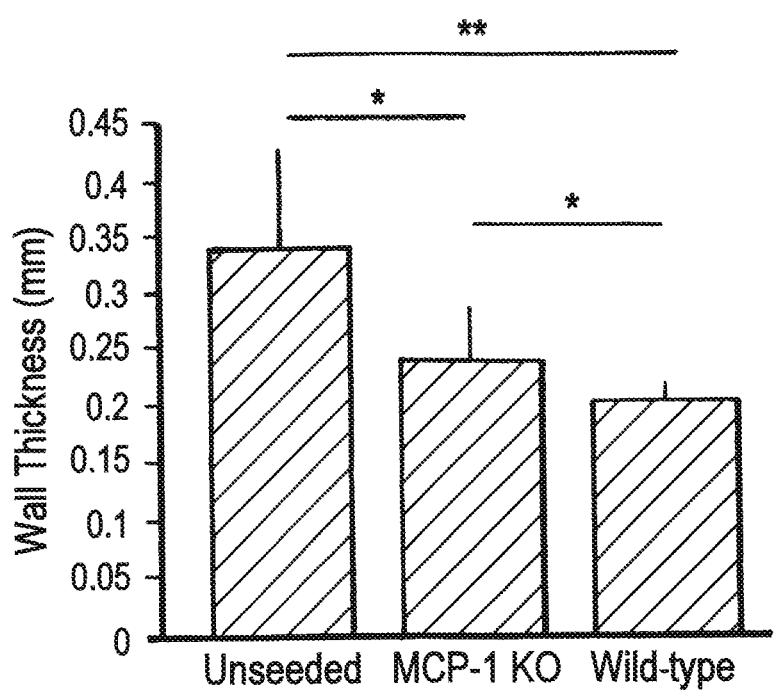
FIG. 5B is a bar graph showing the wall thickness (mm) of TEVGs at 10 weeks after implantation. TEVGs were unseeded, seeded with BMCs from wild-type mice, or seeded with cells from MCP-1 knockout mice.

Knowing that MCP-1 is a potent stimulant for monocyte recruitment, the next series of experiments was performed to determine if the MCP-1 produced by the seeded BMC was important in TEVG development. To analyze the effects of BMC-derived MCP-1, scaffolds were seeded with murine BMC (mBMC) obtained from either MCP-1-/- mice or syngeneic C57BL/6 wild type (WT) mice. BMC from MCP-1-/- mice are unable to produce MCP-1, which specifically eliminates the role of MCP-1 secreted from seeded BMC. After 10 wks of development as IVC interposition grafts in the SCID/bg mouse, MCP-1-/- mBMC-seeded scaffolds (n=5) were compared to WT mBMC-seeded scaffolds (n=5). Internal lumen diameters were decreased, with a trend towards significance (0.55±0.12 mm vs. 0.71±0.12 mm; p=0.07) and graft wall thicknesses were significantly increased (0.25±0.04 mm vs. 0.20±0.01 mm; p=0.04) in scaffolds seeded with MCP-1-/-BMC, suggesting that seeded BMC-derived MCP-1 was playing a critical role in TEVG development (FIGS. 5A and 5B).

Example 5. MCP-1 Microparticles Mimic Paracrine Function of Seeded hBMCs

Materials and Methods:

Materials and methods were as described in Examples 1-4 except as described below.

Synthesis of MCP-1 Eluting Materials

Recombinant human MCP-1 (R&D Systems) was encapsulated into biodegradable alginate microparticles using previously published methods (Jay, et al., *FASEB Jour.*, (2008)). Microparticles were incorporated into the scaffold by directly mixing them into the P(CL/LA) sealant at a concentration of 50 ug/ul. Scaffolds were then constructed using similar methods to those described above. The size and shape distribution of the MCP-1 microparticles, on and off the scaffold, were imaged using a XL-30 scanning electron microscope (FEI Company). The release profile of MCP-1 from these scaffolds was measured by ELBA (R&D Systems). MCP-1 eluting scaffolds (n=5) were each immersed in 1 ml of M199 medium and incubated in a 37° C. orbital shaker. At 1, 2, 4, 8, 12, 24, 48, 72, 96, 120, 144, and 168 hours, medium was collected and replaced with 1 ml of fresh M199 medium. Media samples were stored at −20° C. until analysis.

Figure 6:
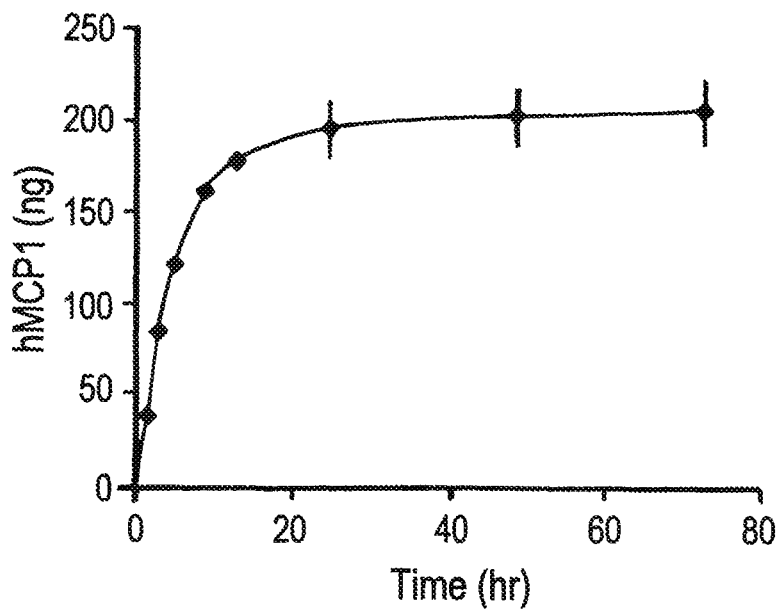
FIG. 6 is a line graph showing the release profile of MCP-1 (ng) from MCP-1 eluting scaffolds as a function of time (hours).

Results:

To investigate whether MCP-1, administered alone, could effectively induce early monocyte recruitment and improve outcomes for unseeded scaffolds, a system was created that enabled delivery of MCP-1 directly from the scaffold without seeding hBMC. Recombinant human MCP-1 was encapsulated into biodegradable alginate microparticles, 1-20 μm in diameter, making them comparable in size to the heterogeneous population of hBMC. The microparticles were then embedded into the scaffold to mimic the MCP-1 releasing function of seeded hBMC. Embedded microparticles released approximately 200 ng of MCP-1 from the scaffold over the course of 72 hours, which was similar to the duration of retention of the majority of seeded hBMC (FIG. 6).

Figure 7A:
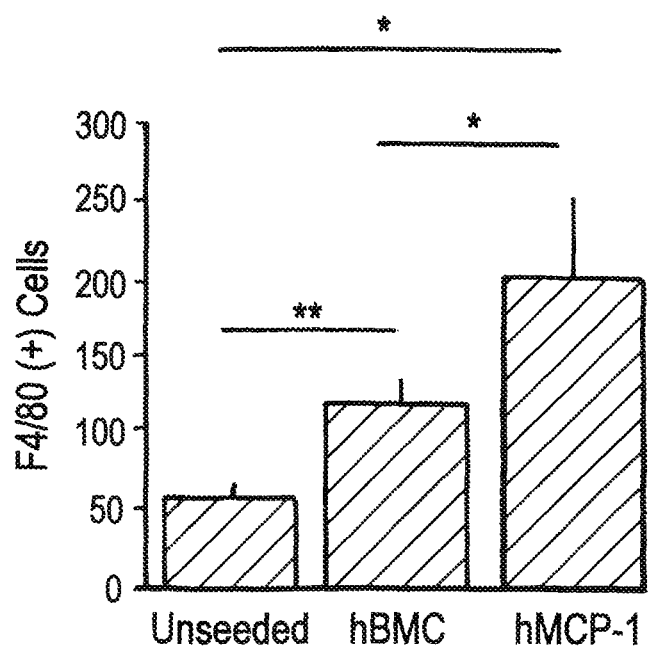
FIG. 7A is a bar graph showing the number of F4/80 positive mouse monocytes/macrophages per scaffold at week 1 following scaffold implantation.
Figure 7B:
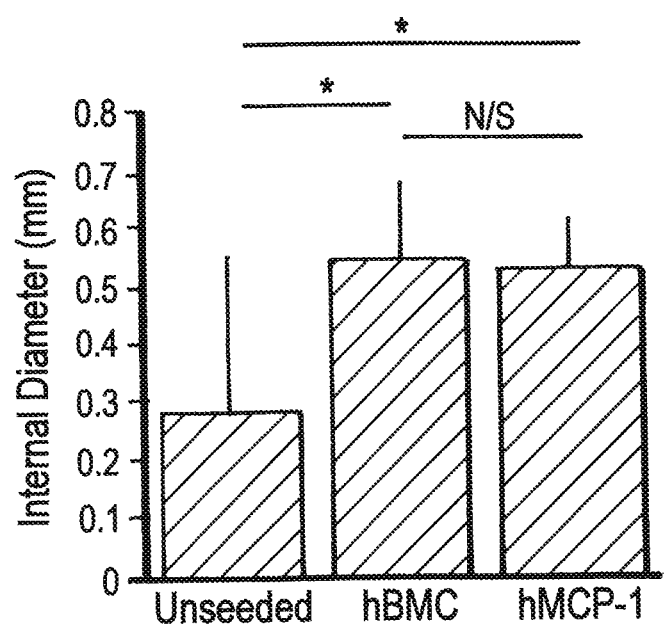
FIG. 7B is a bar graph showing the internal diameter (mm) of scaffolds at 10 weeks after implantation.
Figure 7C:
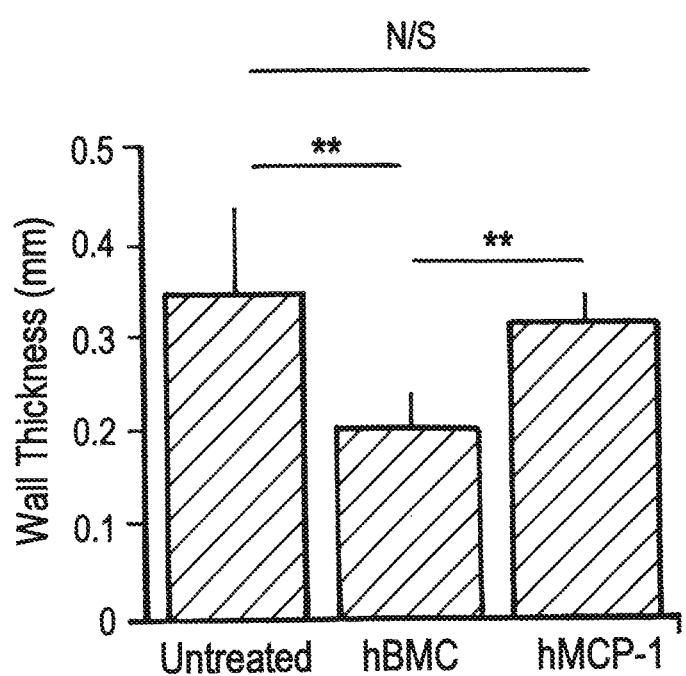
FIG. 7C is a bar graph showing the wall thickness (mm) of scaffolds at 10 weeks after implantation. Scaffolds were unseeded, seeded with hBMCs, or unseeded with MCP-1 eluting microspheres.

Unseeded scaffolds embedded with MCP-1 microparticles developed and functioned similarly to hBMC-seeded scaffolds when implanted as IVC interposition grafts in SCID/bg mice. Host monocyte recruitment at 1 week was significantly increased in MCP-1 eluting scaffolds (n=3; 201±62 monocytes/hpf), compared to both hBMC-seeded (n=6; 120±17 monocytes/hpf; p<0.01) and unseeded (n=4; 60±12 monocytes/hpf; p<0.01) scaffolds (FIG. 7A). Furthermore, after 10 weeks of development, all MCP-1 eluting scaffolds (n=5) were patent with internal lumen diameters comparable to hBMC-seeded scaffolds (n=7) (0.53±0.08 mm vs. 0.63±0.19 mm; p=0.30) (FIG. 7B). Both the seeded scaffolds and those with MCP-1 eluting abilities had better patency rates than the unseeded scaffolds. While MCP-1 microparticles did maintain the internal luminal structure, the wall thickness of MCP-1 eluting scaffolds (0.31±0.02 mm) was more comparable to unseeded scaffolds (0.35±0.10 mm; p=0.48) than hBMC-seeded scaffold (0.20±0.03 mm; p<0.001) (FIG. 7C).

Example 6: G-CSF Administration Promotes Early Outward Remodeling in TEVG

Materials and Methods:

Materials and methods were as described in Examples 1-5 except as described below.

G-CSF Administration

Unseeded scaffolds were implanted as IVC interposition grafts and serially monitored with ultrasound over an 8-week time course. The experimental group received preoperative administration of G-CSF (10 µg/kg) while the control group did not.

Ultrasound Interrogation

Ultrasonography was utilized to serially examine functional and morphologic changes of tissue engineering graft. Mice were anesthetized with 1.5% isoflurane. The internal diameter and wall thickness will be serially measured at longitudinal section of the graft using Vevo 770 (Visualsonics) over the described time course. Measurements were obtained at three locations including measurements at the proximal, middle and distal thirds of the graft in addition to a specific measurement at the narrowest and widest portion of the graft. All measurements were performed by a single operator with expertise in mouse vascular ultrasonography and repeated in triplicate to minimize operator dependent variation.

Statistical Analysis

All data are presented as mean±SEM. Statistical significance was calculated in MS Excel and SPSS 11.5 for Windows. In all multi-group analysis overall comparisons between groups were performed with the one-way ANOVA. If a significant difference was found, pair-wise comparisons were carried out using the Tukey's test, correcting for multiple pair-wise analysis. For strictly pair-wise comparisons, independent student's t-test was carried out. Probability values less than 0.05 were regarded as significant.

Figure 8A:
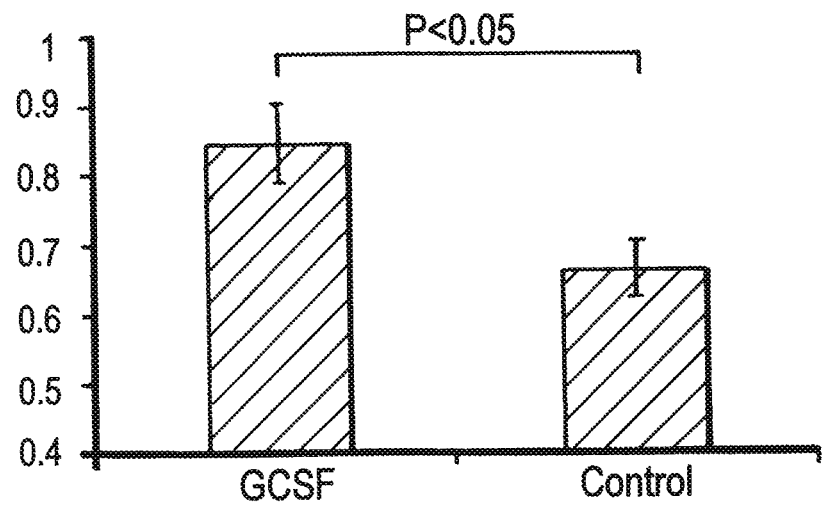
FIG. 8A is a bar graph showing the internal diameter (mm) of scaffolds at 10 weeks after implantation for mice treated with G-CSF or untreated.
Figure 8B:
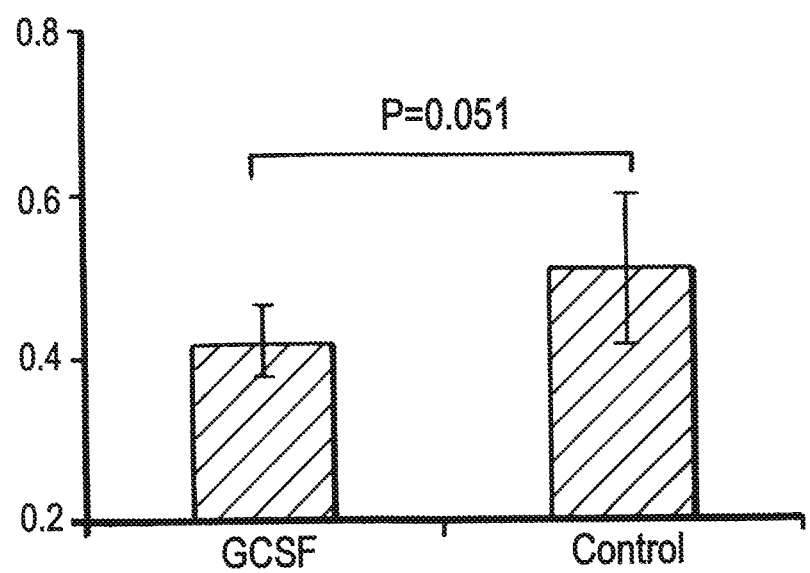
FIG. 8B is a bar graph showing the wall thickness (mm) of scaffolds at 10 weeks after implantation for mice treated with G-CSF or untreated.

Results:

Preoperative administration of G-CSF promotes outward remodeling. Serial ultrasound monitoring demonstrated significantly wider lumens at all time points between 2 and 8 weeks after implantation. These findings were most marked at 4 weeks when the G-CSF group internal diameter measured 0.84 mm±0.06 mm and the control group measured 0.68 mm±0.05 mm (p<0.05) (FIGS. 8A and 8B).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A biodegradable polymeric vascular graft comprising monocyte chemoattractant protein 1 (MCP-1) which is released in an amount between greater than zero and 200 ng per day from the time of implantation and over a period of one week or less effective to recruit an effective amount of host monocytes to the graft to promote neotissue formation at the site of implantation with reduced stenosis and increased patency of the graft in the host over time relative to the patency of the graft in the absence of the MCP-1.

2. The polymeric vascular graft of claim 1, wherein the biodegradable or bioabsorbable polymers are selected from the group consisting of poly (lactic acid), poly (glycolic acid), polyanhydrides, poly (ortho) esters, polyesters, polyurethanes, poly (butic acid), poly (valeric acid), poly (caprolactone), poly (hydroxyalkanoates), poly (lactide-copcaprolactone), and poly (lactide-co-glycolide).

3. The polymeric vascular graft of claim 2, wherein the fiber-based mesh is a non-woven mesh.

4. The polymeric vascular graft of claim 3, wherein the vascular graft further comprises a polymeric sealant.

5. The polymeric vascular graft of claim 4, wherein the polymeric sealant comprises a co-polymer of ε-caprolactone and L-lactide.

6. The polymeric vascular graft of claim 4 wherein the graft is formed of knitted or braided fibers.

7. The polymeric vascular graft of claim 4 wherein the graft is formed of a woven mesh.

8. The polymeric vascular graft of claim 1, further comprising a cytokine or chemokine selected from the group consisting of interleukin (IL) 1α, IL-1β, IL-2, IL-3, IL-4, IL-5, IL-6, IL-7, IL-9, IL-10, IL-12 (p40), IL-12 (p70), IL-13, IL-15, IL-17, IP-10, eotaxin, interferon γ (IFNγ), granulocyte colony-stimulating factor (G-CSF), granulocyte/macrophage colony-stimulating factor (GM-CSF), macrophage inflammatory protein 1α (MIP-1α), RANTES, tumor necrosis factor (TNF)-α, platelet-derived growth factor (PDGF)-AA, PDGF-AB/BB, TGF-beta, VEGF, and combinations thereof.

9. The polymeric vascular graft of claim 1, wherein the vascular graft further comprises an active agent selected from the group consisting of anti-thrombogenic agents, anti-proliferative agents, anti-inflammatory agents, anesthetic agents, anti-coagulants, cholesterol-lowering agents, vasodilating agents, and agents which interfere with endogenous vasoactive mechanisms.

10. The polymeric vascular graft of claim 1, wherein the MCP-1 is dispersed throughout the vascular graft.

11. The polymeric vascular graft of claim 1, wherein the cytokine or chemokine is encapsulated in the form of microspheres, nanospheres, microparticles and/or microcapsules that are seeded into the vascular graft.

12. The polymeric vascular graft of claim 1, wherein the effective amount of MCP-1 is released from microparticles in the graft over a period of 1 to 3 days after the graft is implanted into the host.

13. The polymeric vascular graft of claim 1, wherein the MCP-1 is incorporated into or onto the graft by seeding the graft with microparticles comprising MCP-1 before implantation of the graft into the host.

14. The polymeric vascular graft of claim 1, wherein the graft is seeded with human bone marrow mononuclear cells.

15. The polymeric vascular graft of claim 1, wherein the MCP-1 is provided in microparticles between 1 µm and 20 µm in diameter incorporated into the graft.

16. The polymeric vascular graft of claim 1, wherein the internal diameter of the graft is larger relative to the internal diameter of the graft in the absence of MCP-1 ten weeks after implantation of the graft into the host.

17. The polymeric vascular graft of claim 1, wherein the wall thickness of the graft is thinner relative to the wall thickness of the graft in the absence of MCP-1 ten weeks after implantation of the graft into the host.

18. The polymeric vascular graft of claim 1, for implantation into a pediatric patient.

19. The polymeric vascular graft of claim 1 comprising pores.

20. The polymeric vascular graft of claim 19, wherein the pores are between about 5 μm and about 500 μm in diameter.

21. The polymeric vascular graft of claim 1 wherein the MCP-1 is released over a period of 72 hours.

22. A biodegradable polymeric vascular graft scaffold comprising microparticles encapsulating monocyte chemoattractant protein 1 (MCP-1) which is released immediately after implantation in an amount of greater than zero up to 200 ng for a period of up to one week following graft implantation.

23. The biodegradable polymeric vascular graft scaffold of claim 22 wherein the microparticles are between about one and 20 microns in diameter.

24. The biodegradable polymeric vascular graft scaffold of claim 22 wherein the microparticles release 200 ng MCP-1 over 72 hours.

* * * * *